United States Patent [19]

McLaughlin

[11] 4,130,118
[45] Dec. 19, 1978

[54] CARTRIDGE DISPENSER FOR MEDICATING DOUCHE
[75] Inventor: Jack E. McLaughlin, Yuba City, Calif.
[73] Assignee: Andermac, Inc., Yuba City, Calif.
[21] Appl. No.: 800,390
[22] Filed: May 25, 1977
[51] Int. Cl.² .............................................. A61M 3/00
[52] U.S. Cl. .................... 128/229; 128/239; 128/247
[58] Field of Search ............... 128/224, 247, 229, 239, 128/66, 251; 222/498, 526, 544

[56] References Cited
U.S. PATENT DOCUMENTS

| | | | |
|---|---|---|---|
| 3,373,744 | 3/1968 | Kendall | 128/229 |
| 3,399,676 | 9/1968 | McLaughlin | 128/229 |
| 3,847,150 | 11/1974 | Scheuermann | 128/229 |

Primary Examiner—John D. Yasko
Attorney, Agent, or Firm—Townsend and Townsend

[57] ABSTRACT

This invention relates to improved apparatus for mixing and dispensing a temperature controlled medicated douche from any source of water under pressure. Means are included for maintaining the solution thus discharged at a substantially uniform concentration throughout the entire flow of the solution, which means includes a cartridge of solid water-soluble medicament disposed in the flow path. The cartridge is shaped so as to present a substantially constant surface area in contact with the water flowing past it during all stages of the dissolution of the medicament. Means are also included so that the flow of water cannot occur unless a medicament cartridge is in place.

15 Claims, 4 Drawing Figures

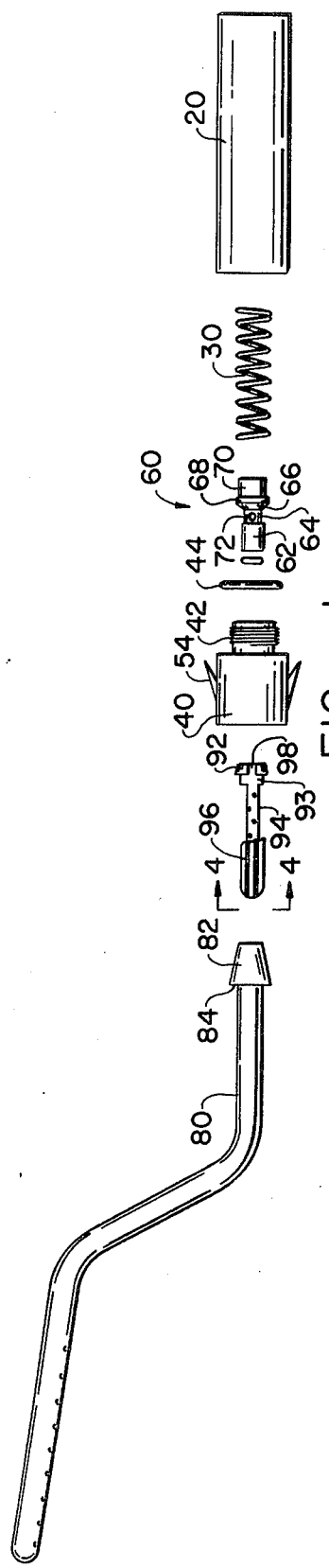
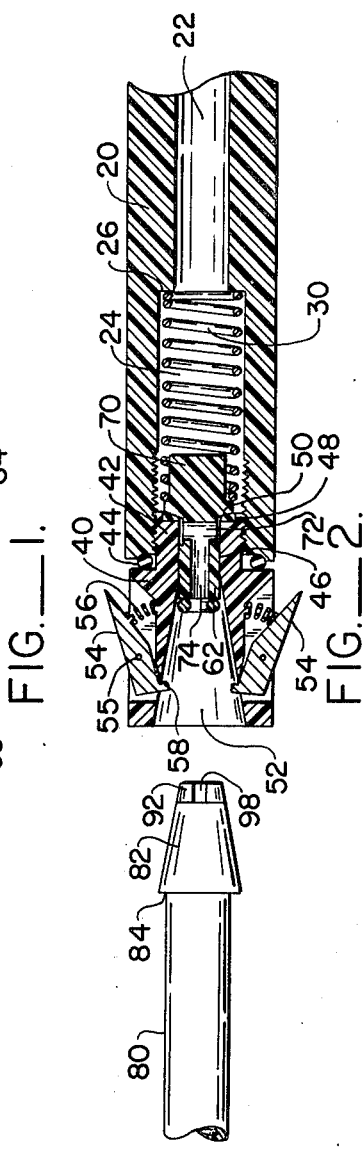
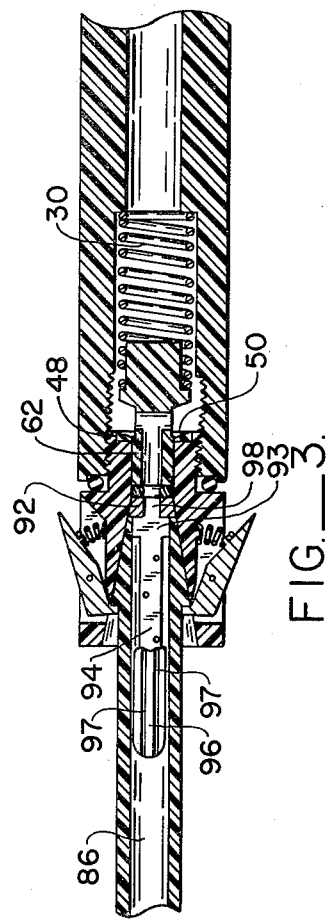
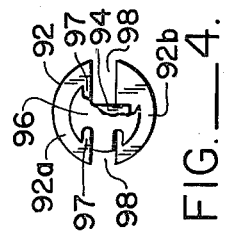

CARTRIDGE DISPENSER FOR MEDICATING DOUCHE

SUMMARY OF THE PRIOR ART

A douche suitable for use by patients is disclosed in U.S. Pat. No. 3,399,676, issued Sept. 3, 1968, invented by me, which disclosure is hereby incorporated by reference. In addition, means for providing a temperature-controlled, pressure-regulated flow of water were described. In my prior invention, the actual mixing of the medicated solution occurred within the handle of the device, said handle being connected at one end to the temperature-controlled, pressure-regulated water source, and at the other end to a removable applicator nozzle. The handle was equipped with finger actuatable valve means to control the flow of water into the handle. The medicament was in the form of a cylindrical cartridge which was inserted in the chamber within the handle, said chamber being directly in the flow path.

The cartridge consisted of a cylindrical shell of water impervious material within which was the solid medicament. The solid medicament was formed so as to contact the inner surface of the shell and provide an axial passageway through which the water would flow. The shape of the passageway was such that the surface area of medicament in contact with the flowing water was substantially constant throughout the period during which the medicament was being dissolved. The shape disclosed was such that a cross section perpendicular to the axis was a six-pointed star.

Access to the cartridge chamber was provided by having the handle screw apart with the line of separation at a point intermediate the ends of the chamber. In order to avoid the possibility of accidentally depressing the valve actuating button during disassembly of the handle during the replacement of the cartridge, or during reassembly of the handle, interlocking means consisting of a finger actuatable slide were provided.

The removable applicator nozzle had a tapered head adapted to fit a complementary tapered recess at the end of the handle. The nozzle was held in place by a threaded collar which fitted over and around the tapered head.

STATEMENT OF THE PROBLEM

Several problems with the prior art device are evident, and it is to these that the improvements of the present invention are directed.

One of the major difficulties with the prior art cartridge is the economic manufacture of the cartridge. Casting an undissolved body of medicament on the inner wall of a cylindrical shell of a cartridge has proved to be mechanically difficult, at best. Moreover, making certain that the medicament adheres to the inner wall of the cylinder has not always been possible.

A second problem with the prior art device is that there is no way of ensuring that a medicament cartridge is in place before use. Since inspection and replacement involve the partial disassembly of the handle, it is a common occurrence for the user to forget to put in a new cartridge.

A third problem with the prior art device is that the handle is made relatively complex in order to provide access to the cartridge chamber and still maintain a liquid-tight seal. Thus, the interlocking slide, the O-ring seal, and the threaded members represent additional fabrication costs and extra potential sources of failure.

A fourth problem with the prior art device relates to the method of attaching the applicator nozzle to the handle. The use of a separate threaded retaining collar leads to at least three potential problems. First, the collar is a separate small part and is easily lost. Second, the collar must be slid over the entire applicator. This increases the chance of contamination of the applicator nozzle due to the increased handling thereof and due to contact with the possibly unhygienic collar. This latter consideration might be quite serious in the event that several people are using the same handle but with individual applicator nozzles. Third, the manipulations of sliding the collar over the applicator and threading it onto the handle may present difficulties for elderly and/or arthritic users of the device.

SUMMARY OF THE INVENTION

This invention relates to improved apparatus for mixing and dispensing a temperature controlled medicated douche from any source of water under pressure. Means are included for maintaining the solution thus discharged at a substantially uniform concentration throughout the entire flow of the solution, which means includes a cartridge of solid water-soluble medicament disposed in the flow path. The cartridge is shaped so as to present a substantially constant surface area in contact with the water flowing past it during all stages of the dissolution of the medicament.

The cartridge slides into the applicator nozzle at the end that attaches to the handle and is held rigidly in place when the nozzle is attached to the handle. The shape of the cartridge is such that the water flows around its outer surface rather than through an axial bore (i.e., it is solid rather than hollow). The actual construction of the cartridge has the medicament cast onto and around an elongate perforated tongue. In this configuration, the cast medicament bonds to itself and to the tongue, thus imparting considerable mechanical strength and structural integrity to the cartridge.

Means are also included so that the flow of water cannot occur unless a medicament cartridge is in place. This is accomplished by having the base of the tongue form an extension of the tapered head of the applicator nozzle when the cartridge is inserted into the applicator nozzle. This extension contacts a spring-loaded valve member at the end of the flow path in the handle, and holds the valve in an open position so long as the nozzle is properly connected to the handle. The tapered head without the extension effected by the placement of the cartridge does not contact the valve, with the result that the valve remains in its normally closed position and no flow is possible.

OBJECTS OF THE INVENTION

One of the objects of this invention is to provide apparatus for mixing and dispensing a medicated douche, which apparatus is simple, compact, rugged, and suitable for home use.

Another object of this invention is the provision of apparatus to dispense a medicated aqueous solution whose concentration is not subject to sudden variations and is substantially free of undissolved medicament.

A further object is the provision of an improved discharge handle that has a minimum of moving parts and points requiring a liquid-tight seal.

A still further object is the provision of apparatus for dispensing a medicated douche where the applicator nozzle and/or medicament cartridge may be safely changed while the water to the handle is maintained under pressure.

Yet another object is the provision of means whereby the flow of water is automatically interrupted if there is no medicament cartridge in place.

Other objects and advantages will become clear upon examination of the drawings and their description.

BRIEF DESCRIPTION OF THE DRAWINGS

FIG. 1 is an exploded view of those portions of the apparatus that go to making up the claimed improvements;

FIG. 2 is a sectional side view of the discharge end of the handle showing the internal valve means for blocking the flow of water when either the applicator nozzle or medicament cartridge is not in place;

FIG. 3 is a sectional side view of the discharge end of the handle and the head end of the applicator nozzle with the nozzle and medicament cartridge in place. This figure shows how the base of the cartridge holds the internal valve means open to permit the flow of water past the cartridge; and, FIG. 4 is a sectional, partly cut away end view of the medicament cartridge.

DETAILED DESCRIPTION OF THE DRAWINGS

FIG. 1 is an exploded view of those portions of the apparatus that relate to the connection of the applicator nozzle to the discharge end of the handle and to the insertion of the medicament cartridge in said discharge nozzle. The means for providing the temperature controlled, pressure regulated flow of water, and the finger actuated valve means for controlling such flow are fully described in the above referenced U.S. Pat. No. 3,399,676 and will not be described herein.

FIG. 2 is a sectional view of most of the parts shown in FIG. 1. The part 20 of the handle that is nearest the nozzle is formed with a bore 22 through which water flows. The part 20 is counterbored from the downstream end to provide a bore 24 that is coaxial with bore 22 and of a slightly larger diameter. The counterbore 24 is made with a flat bottom so as to provide a downstream-facing shoulder 26 for valve spring 30 to bottom against.

The downstream end of counterbore 24 is tapped so as to receive the threaded portion 42 of part 40, which part provides a seat for valve member 60 and means to hold the applicator nozzle 80 in place. A liquid-tight seal between parts 20 and 40 is provided by O-ring 44.

The upstream end of part 40 is formed with a cylindrical bore 46. Part 40 is counterbored from the upstream end to provide a portion 48 that is coaxial with bore 46 and of a depth and diameter to accept and retain a tapered washer 50 that has an inner diameter when in place substantially that of bore 46. Tapered washer 50 serves as a seat for valve member 60. In an alternate embodiment, an O-ring may be used instead of tapered washer 50.

The downstream portion of part 40 is formed with a tapered recess 52 which is coaxial with bore 46 and begins at the downstream end with a diameter larger than that of bore 46. This recess is uniformly reduced proceeding upstream so that it is of the same diameter as bore 46 at a point intermediate the ends of part 40. In an alternate embodiment, not shown, tapered recess 52 is truncated when its diameter is still slightly larger than that of bore 46 so that there is a small downstream-facing shoulder where recess 52 meets bore 46.

Each of two pivoted latches 54 is loaded on one side of the pivot 55 by spring 56 so that inwardly directed protrusion 58 on the other side of pivot 55 extends into the tapered recess 52. The ends of the latches 54 remote from the protrusions 58 extend outside the outer diameter of part 40. Thus inward finger pressure of a squeezing nature on the latches acts in opposition to the forces of springs 56 and causes the protrusions to move out of the tapered recess 52.

Valve member 60 consists of five structural elements, each of which possesses cylindrical symmetry, and all of which are coaxial with one another. Therefore valve member 60 may be fabricated as a single turning. Proceeding from the downstream end, these five elements are as follows.

Cylindrical portion 62 has a diameter substantially that of bore 46, but just enough smaller so that said portion 62 can reciprocate freely within said bore 46.

Cylindrical portion 64 has a diameter slightly less than that of portion 62 so that there is no contact between valve member 60 and tapered washer 50 while portion 62 reciprocates within bore 46.

Frustroconical portion 66 has its larger diameter at the upstream end, and is that part of valve member 60 that actually seats against tapered washer 50. Thus the larger diameter is by necessity larger than that of portion 62. The relative lengths of portions 62 and 64, and bore 46 are such that when frustroconical portion 68 seats against tapered washer 50, portion 62 extends into tapered recess 52.

Two further cylindrical portions, a cylindrical portion 68 having a diameter equal to that of the larger diameter of frustroconical portion 66, and a cylindrical portion 70 having a diameter smaller that that of portion 68 and of a size to fit inside valve spring 30, form an upstream-facing shoulder for spring 30 to bear against.

Cylindrical portion 64 has a transverse bore 72 extending clear through said portion. Valve member 60 is counterbored from the downstream end to provide a bore 74 coaxial with valve member 60, which bore extends axially through cylindrical portion 62, and into cylindrical portion 64 to that depth at which it meets transverse bore 72. Thus there is a T-shaped hollow within valve member 60, which hollow communicates to the outside of valve member 60 at all three ends of the "T."

The functioning of valve member 60 can now be understood. So long as no upstream force is exerted on the part of cylindrical portion 62 that extends into tapered recess 52, spring 30 keeps the frustroconical portion 66 seated against tapered washer 50. No fluid flow can occur past valve member 60 since it is solid except for the two bores 72 and 74 described above. However, if valve member 60 is displaced upstream, which displacement occurs against the force exerted by spring 30, fluid under pressure can flow between frustroconical portion 66 and tapered washer 50, flow into transverse bore 72 from both ends, pass through bore 74, and exit said bore 74.

Applicator nozzle 80 is described in the above referenced U.S. Pat. No. 3,399,676 and only those parts directly applicable to the present improvement will be described herein.

The applicator nozzle consists of a hollow tube 80 which is closed at its downstream end and perforated along at least part of its length. The nozzle is formed at its upstream end with a frustroconical head 82 and outer surface of which is complementary with tapered recess 52. Said head meets tube 80 so as to form a downstream-facing shoulder 84. The smaller diameter of head 82 is such that head 82 does not touch the downstream end of cylindrical portion 62 of valve member 60 when said head is fully inserted into said tapered recess. The larger diameter of head 82 is determined by the requirement that the protrusions 58 of latches 54 engage the downstream facing shoulder 84 when the head is fully inserted into the tapered recess and that they hold the head tightly in place. The bore 86 of tube 80 extends through head 82.

The medicament cartridge consists of three basic elements: a slotted frustroconical base 92; an elongate perforated tongue 94; and a cohesive mass of solid medicament 96 cast onto and around tongue 94. The maximum transverse dimension of the cast medicament 96 is such that it fits loosely within bore 86.

The larger diameter of cartridge base 92 is larger than that of bore 86, and in the embodiment shown is the same as the smaller diameter of frustroconical head 82. Furthermore, the degree of taper of base 92 conforms to that of head 82, so that the base in effect forms an extension of the head when the cartridge is inserted in the nozzle. FIG. 3 shows the effect of inserting the applicator nozzle into tapered recess 52 when a medicament cartridge is in place. In particular, base 92 bears against the end of cylindrical portion 62 of valve member 60 that extends into tapered recess 52. In this manner the force of spring 30 is overcome and valve member 60 is forced into the open position. To make fluid flow possible, the frustroconical base 92 is slotted. Referring to the side view of FIGS. 1, 2 and 3 and the end view in FIG. 4, it is seen that two relatively wide and deep slots 98 parallel to the axis are provided. Thus the base closely resembles two discrete segments 92a and 92b joined by a thin web 93, the extension of which web is tongue 94.

Tongue 94 forms the central strength giving core of the medicament cartridge. The tongue is perforated, with resulting improved adhesion of the medicament to the tongue. The improved adhesion arises out of two main effects. First, the holes give rise to a surface with increased irregularity. Second, the medicament fills the holes and thus has a greater opportunity to bond to itself and thereby resist flaking.

The mass of medicament 96 has a cylindrical form surrounding tongue 94. Longitudinal grooves 97 are employed to produce a shape that maintains a more nearly constant surface area as the outer layer of medicament is dissolved. This minimizes the variation in concentration during the period that medicament is being dissolved. As can be seen in FIG. 4 the opposing grooves and the adjacent grooves are all parallel to one another. The grooves are rounded at the bottom and the side walls may be made to converge slightly toward the bottom so as to facilitate the casting of the mass of medicament.

I claim:

1. In apparatus for making and dispensing an aqueous cleansing, sanitizing, and treating solution for application to body tissue within a body cavity, which apparatus contains a dispensing handle, an applicator nozzle, a cartridge containing water-soluble salts, and at least one normally closed valve, wherein said handle and said nozzle each defines separate portions of a conduit for the passage of water and said portions together define said conduit, the combination comprising: said cartridge disposed in said conduit; and means connecting said cartridge and said valve enabling said valve to open only if said cartridge is in place in said conduit.

2. The invention of claim 1 wherein said means connecting said cartridge and said valve enabling said valve to open only if said cartridge is in place in said conduit enable said valve to open only if said nozzle is connected to said handle.

3. The invention of claim 1 wherein there are first and second normally closed valves, the first of which is opened by said means connecting said cartridge, and the second of which is manually actuated.

4. The invention of claim 3 wherein said second valve is located in said handle.

5. The invention of claim 1 wherein the water soluble portion of said cartridge is disposed in that portion of said conduit defined by said nozzle.

6. The invention of claim 1 wherein the water soluble portion of said cartridge is disposed in that portion of said conduit defined by said handle.

7. The invention of claim 1 wherein the fixed positioning of said cartridge can occur only if said nozzle and said handle are connected.

8. The invention of claim 1 wherein said valve is maintained in its normally closed position by a spring.

9. The invention of claim 1 wherein said means for connecting said cartridge and said valve comprise a member of said cartridge.

10. In apparatus for making and dispensing an aqueous cleansing, sanitizing, and treating solution for application to body tissue within a body cavity, a cartridge comprising: an elongate strip of water impervious material, said strip having a plurality of holes through the smaller of the two transverse dimensions; and a body of water soluble salts formed about said elongate strip, said body of salts being cohesively bound within itself, said salts being bonded to the surfaces of said strip, said salts filling said holes in said strip whereby those of said salts on opposite sides of said strip are afforded the opportunity of bonding to one another through said holes, said body of salts having a cross-section that is substantially constant from end to end, the outer surface of said body of salts being shaped to present a substantially constant surface area to a stream of water flowing by said body during the time that said salts are being dissolved by and into said stream of water whereby the rate of dissolution of said salts is substantially constant during said time.

11. The invention of claim 10 wherein said body of salts is substantially cylindrical in overall contour, and is formed with a plurality of longitudinal grooves, said grooves extending inwardly from the surface of said cylindrical contour in a plane perpendicular to that in which said strip lies.

12. The invention of claim 10 wherein one end of said strip terminates on a base of water impervious material, said base being capable of being rigidly clamped to hold said cartridge in a fixed position within said apparatus.

13. In apparatus for making and dispensing an aqueous cleansing, sanitizing, and treating solution for application to body tissue within a body cavity, which apparatus contains a dispensing handle, an applicator nozzle, and a cartridge containing water soluble salts, wherein said handle and said nozzle each defines separate portions of a conduit for the passage of water and said portions together define said conduit, the improvement comprising: a normally closed valve in said conduit; and means enabling the conduit to be opened only if said cartridge is in place and said nozzle is connected to said handle.

14. The invention of claim 13 wherein said enabling means holds said valve open.

15. In apparatus for making and dispensing an aqueous cleansing, sanitizing, and treating solution for application to body tissue within a body cavity, which apparatus contains a dispensing handle, an applicator nozzle, a cartridge containing water soluble salts, and a finger actuatable valve on said handle, wherein said handle and said nozzle each defines separate portions of a conduit for the passage of water and said portions together define said conduit, an improved cartridge comprising: an elongate strip of water impervious material, said strip having a plurality of holes through the smaller of the two transverse dimensions; and a body of water soluble salts formed about said elongate strip, said body of salts being cohesively bound within itself, said salts being bonded to the surfaces of said strip, said salts filling said holes in said strip whereby those of said salts on opposite sides of said strip are afforded the opportunity of bonding to one another through said holes, said body of salts having a cross-section that is substantially constant from end to end, the outer surface of said body of salts being shaped to present a substantially constant surface area to a stream of water flowing by said body during the time that said salts are being dissolved by and into said stream of water whereby the rate of dissolution of said salts is substantially constant during said time.

* * * * *